United States Patent [19]
Panayotatos

[11] Patent Number: 4,716,112
[45] Date of Patent: Dec. 29, 1987

[54] VECTORS FOR INCREASED EXPRESSION OF CLONED GENES

[75] Inventor: Nikos Panayotatos, Geneva, Switzerland

[73] Assignee: Biogen N.V., Curacao, Netherlands Antilles

[21] Appl. No.: 829,456

[22] Filed: Feb. 11, 1986

Related U.S. Application Data

[63] Continuation of Ser. No. 531,235, Sep. 12, 1983, abandoned.

[30] Foreign Application Priority Data

Sep. 16, 1982 [GB] United Kingdom ............... 8226409

[51] Int. Cl.$^4$ ................. C12P 21/00; C12N 15/00; C12N 1/20; C12N 1/00
[52] U.S. Cl. .................... 435/68; 435/172.3; 435/253; 435/320; 935/41; 935/42; 935/29; 935/60
[58] Field of Search .............. 435/68, 253, 172.3, 435/317; 935/41, 42, 60, 29

[56] References Cited

U.S. PATENT DOCUMENTS

4,332,892  6/1982  Ptashne et al. .................... 435/68

FOREIGN PATENT DOCUMENTS

| 0003062 | 12/1978 | European Pat. Off. |
| 0022242 | 7/1980 | European Pat. Off. |
| 0041767 | 4/1981 | European Pat. Off. |
| 0048497 | 9/1981 | European Pat. Off. |
| 0060045 | 2/1982 | European Pat. Off. |
| 0068740 | 6/1982 | European Pat. Off. |
| 0073656 | 8/1982 | European Pat. Off. |
| 0076037 | 8/1982 | European Pat. Off. |
| 0013830 | 1/1983 | European Pat. Off. |

OTHER PUBLICATIONS

Bernard et al, 1979, "Construction of Plasmid Cloning Vehicles that Promote Gene Expression from the Bacteriophage Lambda P$_L$ Promoter Gene, v5, 59-76.
Panayotatos et al, 1981, "Specific Deletion of DNA Sequences Between Preselected Bases", Nucleic Acids Res., vol. 9 (21), pp. 5679-5688.
Sutcliffe, 1979, "Complete Nucleotide Sequence of the E. coli Plasmid pBR 322", Cold Spring Harbor Symp. Quant. Biol., v. 43, pp. 77-90.
Tomizawa et al., 1981, "Plasmid ColE1 Incompatibility Determined by Interaction of RNA1 with Primer Transcript", Proc. Natl Acad Sci USA, vol. 78, No. 10, pp. 6096-6100.
Wong et al, 1982, "Temperature-Sensitive Copy Number Mutants of ColE1 are Located in an Untranslated Region of the Plasmid Genome", Proc. Nat'l Acad. Sci. USA, vol. 79, pp. 3570-3574.
Muesing et al, 1981, "A Single Base-Pair Alteration is Responsible for the DNA Overproduction Phenotype of a Plasmid Copy-Number Mutant", Cell, v. 24, pp. 235-242.

(List continued on next page.)

Primary Examiner—Thomas G. Wiseman
Assistant Examiner—Karen Maurey
Attorney, Agent, or Firm—James F. Haley, Jr.; Denise L. Loring

[57] ABSTRACT

Improved expression vectors for amplifying expression of DNA sequence encoding a desired polypeptide beyond that expected by the vector copy number. The vector contains a DNA sequence within the replicon of the vector encoding RNA I and the primer RNA for initiation of DNA replication and their regulatory regions, said DNA sequence having an AT to GC mutation at position 3029 in the two strands of pBR322; a promoter of RNA I or primer RNA and a restriction site for insertion of a DNA sequence encoding a desired polypeptide into the vector and operatively linking the DNA sequence to the expression control sequence. The AT to GC mutation causes an increase in the vector copy number and further amplifies the expression of the desired polypeptide operatively linked to the RNA I or primer RNA promoter beyond that expected by the copy number increase.

8 Claims, 5 Drawing Figures

OTHER PUBLICATIONS

Panayotatos et al, 1979, "Cloning and Localization of the *in vitro* Functional Origin of Replication of Bacteriophage T7 DNA", J. Biol. Chem., v. 254, (12) pp. 5555–5560.

Wong, E. M. et al., *Proc Natl Acad Sci USA*, 79:3570–3574, 1982.

Panayotatos, N., *Nucleic Acids Research*, 9(21):5679–5688, 1981.

Tomizawa, J., et al, *Proc Natl Acad Sci USA* 78(10) 6096–6100.

Stuitje, A. R., et al, *Nature*, 290:264–267, 1981.

Muesing, M., et al, *Cell*, 24: 235–242, 1981.

Backman and Ptashne, "Maximizing Gene Expression on a Plasmid Using Recombination in Vitro, *Cell*, 13, 65–71 (1978).

Bernard et al., "Construction of Plasmid Cloning Vehicles that Promote Gene Expression from the Bacteriophage Lambda $P_L$ Promoter", *Gene*, 5, 59–76 (1979).

Blattner et al., "Charon Phages: Safer Derivatives of Bacteriophage Lambda for DNA Cloning", *Science*, 196, 161–169 (1977).

Cesarini, "The RNA Primer Promoter, as Defined in Vitro, is Essential for pMBI Plasmid Replication in Vivo", *J. Mol. Biol.*, 160, 123–126 (1982).

Charnay et al., "Bacteriophage Lambda and Plasmid Vectors, Allowing Fusion of Cloned Genes in Each of the Three Translational Phases", *Nucleic Acids Research*, 5, 4479–4494 (1978).

Clewell, "Nature of Col $E_1$ Plasmid Replication in Plasmid DNA", *Proc. Natl. Acad. Sci. USA*, 74, 1865–1869 (1977).

Twigg and Sherratt, "Trans–Complementable Copy–-Number Mutants of Plasmid ColE1", *Nature*, 283, 216–218 (1980).

*Escherichia coli* in the Presence of Chloramphenicol", *J. Bacteriol.*, 110, 667–676 (1972).

Conrad and Campbell, "Plasmid DNA Replication", *Cell*, 62–71 (1979).

Kahn et al., "Plasmid Cloning Vehicles Derived from Plasmids ColE1, F, R6K, and RK2", *Methods in Enzymology*, 68, 268–280 (1979).

Lacatena and Cesareni, "Base Pairing of RNA I with its Complementary Sequence in the Primer Precursor Inhibits ColE1 Replication", *Nature*, 294, 623–226 (1981).

O'Farrell et al., "Regulated Expression by Read-through Translation from a Plasmid–Encoded–Galactosidase", *J. Bacteriol.*, 134, 645–654 (1978).

Oka et al., "Nucleotide Sequence of Small ColE1 Derivatives: Structure of the Regions Essential for Autonomous Replication and Colicin E1 Immunity", *Molec. Gen. Genet.*, 172, 151–159 (1979).

Oka and Takanami, "Cleavage Map of Colicin E1 Plasmid", *Nature*, 264, 193–196 (1976).

Roberts and Lauer, "Maximizing Gene Expression on a Plasmid Using Recombination in Vitro, *Methods in Enzymology*, 68, 473–483 (1979).

Roberts et al., "A General Method for Maximizing the Expression of a Cloned Gene", *Proc. Natl. Acad. Sci. USA*, 76, 760–764 (1979).

Remaut et al., "Plasmid Vectors for High-Efficiency Expression Controlled by the $P_L$ Promoter of Coliphage Lambda", *Gene*, 15, 81–93 (1981).

Stuitje et al., "Identification of Mutations Affecting Replication Control of Plasmid Clo DF13", *Nature*, 290, 264–267 (1981).

Tomizawa et al., "Origin of Replication of Colicin E1

VECTORS FOR INCREASED EXPRESSION OF CLONED GENES

This is a continuation of application Ser. No. 531,235, filed Sept. 12, 1983, entitled IMPROVED EXPRESSION VECTORS, now abandoned.

TECHNICAL FIELD OF INVENTION

This invention relates to improved expression vectors and to methods for making such vectors and for expressing cloned genes using them. The vectors and methods disclosed in this invention are characterized by the improved expression of cloned genes, particularly those of eukaryotic origin, in prokaryotic hosts. As will be appreciated from the disclosure to follow, these vectors and methods may be used to improve the production of various polypeptides, proteins and amino acids in host cells.

BACKGROUND ART

The level of production of a protein in a host cell is governed by three major factors: the number of copies of its gene within the cell, the efficiency with which those gene copies are transcribed and the efficiency with which the resultant messenger RNA ("mRNA") is translated. Efficiency of transcription and translation (which together comprise expression) is in turn dependent upon the nucleotide sequences which are normally situated ahead of the desired coding sequence or gene. These nucleotide sequences or expression control sequences define, inter alia, the location at which RNA polymerase interacts (the promoter sequence) to initiate transcription and at which ribosomes bind and interact with the mRNA (the product of transcription) to initiate translation.

Not all such expression control sequences function with equal efficiency. It is thus often of advantage to separate the specific coding sequence or gene for a desired protein from its adjacent nucleotide sequences and to fuse it instead to other expression control sequences so as to favor higher levels of expression. This having been achieved, the newly-engineered DNA fragment may be inserted into a higher copy number plasmid or a bacteriophage derivative in order to increase the number of gene copies within the cell and thereby further to improve the yield of expressed protein.

Because over-production of even normally non-toxic gene products may be harmful to host cells and lead to decreased stability of particular host-vector systems, an expression control sequence, in addition to improving the efficiency of transcription and translation of cloned genes, is also often made controllable so as to modulate expression during bacterial growth. For example, controllable expression control sequences are ones that may be switched off to enable the host cells to propagate without excessive build-up of gene products and then switched on to promote the expression of large amounts of the desired protein products, which are under the control of those expression control sequences.

Several expression control sequences, which satisfy some of the criteria set forth above, have been employed to express DNA sequences and genes coding for proteins and polypeptides in bacterial hosts. These include, for example, the operator, promoter and ribosome binding and interaction sequences of the lactose operon of *E. coli* (e.g., K. Itakura et al., "Expression In *Escherichia coli* Of A Chemically Synthesized Gene For The Hormone Somatostatin", *Science*, 198, pp. 1056–63 (1977); D. V. Goeddel et al., "Expression In *Escherichia coli* Of Chemically Synthesized Genes For Human Insulin", *Proc. Natl. Acad. Sci. USA*, 76, pp. 106–10 (1979)), the corresponding sequences of the tryptophan synthetase system of *E. coli* (J. S. Emtage et al., "Influenza Antigenic Determinants Are Expressed From *Haemagglutinin* Genes Cloned In *Escherichia coli*", *Nature*, 283, pp. 171–74 (1980); J. A. Martial et al., "Human Growth Hormone: Complementary DNA Cloning And Expression In Bacteria", *Science*, 205, pp. 602–06 (1979)) and the major operator and promoter regions of phage λ (H. Bernard et al., "Construction Of Plasmid Cloning Vehicles That Promote Gene Expression From The Bacteriophage Lambda $P_L$ Promoter", *Gene*, 5, pp. 59–76 (1979); European patent application No. 41767).

Promoters for primer RNA and RNA I from the colicin EI genome (Col EI) are also known (E. M. Wong et al., "Temperature-Sensitive Copy Number Mutants Of Col EI Are Located In An Untranslated Region Of The Plasmid Genome", *Proc. Natl. Acad. Sci. USA*, 79, pp. 3570–74 (June 1982)). Among the group of promoters useful in the expression vectors and methods of this invention are these two promoters, i.e., the promoter for primer RNA (hereinafter designated "$P_m$") and the promoter for RNA I (hereinafter designated "$P_I$"). A temperature sensitive copy number mutant of promoter $P_I$ is also known (E. M. Wong et al., supra). This promoter is also among those useful in this invention.

Promoters $P_I$ and $P_m$ are thought to be constitutive, i.e., they are not under the control of repressors, so that they continually promote expression of genes operatively-linked to them. Moreover, promoter $P_m$ may apparently be strengthened by mutation (E. M. Wong et al., supra).

DISCLOSURE OF THE INVENTION

The present invention relates to improved expression vectors and methods for expressing cloned genes. More specifically, it provides expression vectors comprising an expression control sequence characterized by at least one promoter selected from the group consisting of the promoter of RNA I, the promoter of the primer RNA for initiation of DNA replication and derivatives thereof; a DNA sequence within the replicon of the vector encoding RNA I and the primer RNA for initiation of DNA replication and their regulatory regions, said DNA sequence being characterized by at least one modification, said modification increasing the copy number of the vector in an appropriate host as compared to a vector without said modification and further amplifying the expression of genes and DNA sequences under the control of said expression control sequence of said vector; and at least one restriction site wherein a DNA sequence encoding a desired polypeptide may be inserted into said vector and operatively linked therein to said expression control sequence.

More preferably, the expression vectors of this invention comprise an expression control sequence characterized by at least one promoter selected from the group consisting of the promoter of RNA I, the promoter of the primer RNA for the initiation of DNA replication and derivatives thereof; a col EI-derived DNA sequence within the replicon of the vector encoding RNA I and the primer RNA for initiation of DNA replication and their regulatory regions, said DNA sequence being characterized by at least one mutation at position 3029 of pBR322, said mutation increasing the copy number of the vector in an appropriate host about 5 times as compared to a vector without said mutation and further amplifying the expression of genes and DNA sequences under the control of said expression control sequence; and at least one restriction site wherein a DNA sequence encoding a desired polypeptide may be inserted into said vector and operatively linked therein to said expression control sequence.

As will be appreciated from the description of this invention, the expression vectors and methods of this invention permit the high level expression of prokaryotic and eukaryotic products encoded for by DNA sequences inserted into the restriction site of the expression vector of this invention and operatively linked therein to the expression control sequence of that vector in appropriate hosts.

BEST MODE OF CARRYING OUT THE INVENTION

Figure 1:
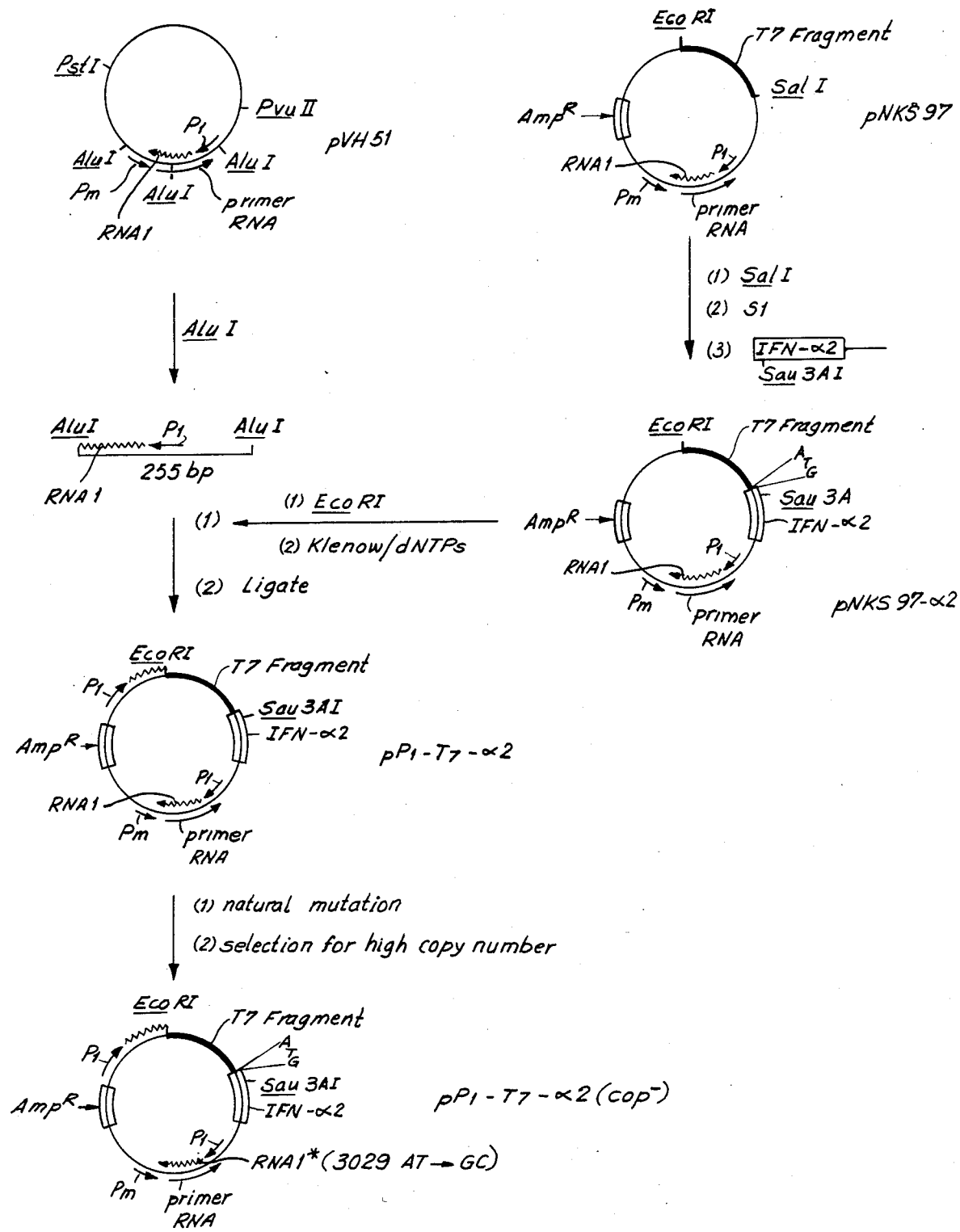
FIG. 1 is a schematic outline of one embodiment of making and using an expression vector of this invention.

In order that the invention herein described may be more fully understood, the following detailed description is set forth.

In the description the following terms are employed:

Nucleotide—A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is called a nucleoside. The base characterizes the nucleotide. The four DNA bases are adenine ("A"), guanine ("G"), cytosine ("C"), and thymine ("T"). The four RNA bases are A, G, C and uracil ("U").

DNA Sequence—A linear array of nucleotides connected one to the other by phosphodiester bonds between the 3' and 5' carbons of adjacent pentoses.

Codon—A DNA sequence of three nucleotides (a triplet) which encodes, through its template or messenger RNA ("mRNA"), an amino acid, a translation start signal or a translation termination signal. For example, the nucleotide triplets TTA, TTG, CTT, CTC, CTA and CTG encode the amino acid leucine ("Leu"), TAG, TAA and TGA are translation stop signals and ATG is a translation start signal.

Polypeptide—A linear array of amino acids connected one to the other by peptide bonds between the α-amino and carboxy groups of adjacent amino acids.

Gene—A DNA sequence which encodes through its mRNA a sequence of amino acids characteristic of a specific polypeptide.

Transcription—The process of producing mRNA from a gene or DNA sequence.

Translation—The process of producing a polypeptide from mRNA.

Expression—The process undergone by a DNA sequence or gene to produce a polypeptide. It is a combination of transcription and translation.

Plasmid—A nonchromosomal, double-stranded DNA sequence comprising an intact "replicon" such that the plasmid is replicated in a host cell. When the plasmid is placed within a unicellular organism, the characteristics of that organism may be changed or transformed as a result of the DNA of the plasmid. For example, a plasmid carrying the gene for tetracycline resistance ($Tet^R$) transforms a cell previously sensitive to tetracycline into one which is resistant to it. A host cell transformed by a plasmid or vector is called a "transformant".

Phage or Bacteriophage—Bacterial virus many of which consist of DNA sequences encapsidated in a protein envelope or coat ("capsid").

Cloning Vehicle or Vector—A plasmid, phage DNA or other DNA sequence which is able to replicate in a host cell, characterized by one or a small number of endonuclease recognition or restriction sites at which such DNA sequences may be cut in a determinable fashion without attendant loss of an essential biological function of the DNA, e.g., replication, production of coat proteins or loss of promoter or binding sites, and which contains a marker suitable for use in the identification of transformed cells, e.g., tetracycline resistance or ampicillin resistance.

Cloning—The process of obtaining a population of organisms or DNA sequences derived from one such organism or sequence by asexual reproduction.

Recombinant DNA Molecule or Hybrid DNA—A molecule consisting of segments of DNA from different genomes (the entire DNA of a cell or virus) which have been joined end-to-end outside of living cells and have the capacity to infect some host cell and to be maintained therein.

Expression Control Sequence—A sequence of nucleotides that controls and regulates expression of genes or DNA sequences when operatively linked to those genes or DNA sequences. The term "operatively-linked" includes having an appropriate start signal in front of the gene or DNA sequence encoding the desired product and maintaining the correct reading frame to permit expression of the inserted DNA sequence under the control of the expression control sequence and production of the desired product encoded for by that gene or DNA sequence.

THE HOST CELLS OF THIS INVENTION

Any of a large number of available and well known host cells may be used in the host-expression vector combinations of this invention. The selection of a particular host is dependent upon a number of factors recognized by the art. These include, for example, compatibility with the chosen expression vector, toxicity of the proteins encoded for by the hybrid plasmid, ease of recovery of the desired protein, expression characteristics, biosafety and costs. A balance of these factors must be struck with the understanding that not all hosts may be equally effective for the expression of a particular DNA sequence in the expression vectors and methods of this invention.

Within these general guidelines, useful hosts may include strains of *E. coli, Pseudomonas, Bacillus,* streptomyces, yeast and other fungi, animal or plants hosts, such as animal (including human) or plant cells in culture or other hosts known in the art.

The most preferred host cell of this invention is *E. coli* HB101. The yields of desired protein production in other *E. coli* strains are lower than in HB101. For example, *E. coli* MC1061 affords much lower yields of the desired protein than does HB101, while other *E. coli* strains afford intermediate yields. This host cell specific effect may be caused by varying levels of protease concentrations in different *E. coli* strains rather than by any real difference in the level of transcription or translation of the desired DNA sequence. Thus, in those strains with high protease concentrations the proteins produced by the method of this invention are presumably degraded more readily, resulting in a smaller apparent level of production.

THE EXPRESSION CONTROL SEQUENCES OF THIS INVENTION

The expression control sequences of this invention are characterized by at least one promoter selected from the group consisting of the promoter of RNA I, the promoter of the primer RNA for DNA replication and derivatives thereof. These first two promoters are hereinafter designated $P_I$ and $P_m$, respectively.

Although in the preferred embodiments of this invention, $P_I$ or $P_m$ are derived from col E1 DNA, the promoters may also be derived from plasmids selected from the group consisting of pBR322, $R_1$, cloDF13 and other similarly organized replicons and their derivatives. The promoters of this invention may also carry a mutation from the wild type promoter that increases the strength of the promoter. Such mutations are known [E. M. Wong et al., supra]. The promoters of this invention may also be combined with other known promoters, such as lac, tac, trp, $P_L$ and combinations thereof.

The expression control sequences of this invention are also characterized by operators, ribosome binding and interaction sequences, such as the Shine-Dalgarno sequences and other DNA sequences related to the regulation of expression of genes and DNA sequences that are operatively linked to those expression control sequences. Such sequences, for example, include sequences from MS2, mu, bacteriophage T7, phage λ, and other like systems. Most preferably, sequences from bacteriophage T7 are employed in the expression vectors of this invention.

The expression vectors of this invention are also characterized by a DNA sequence within the replicon of the vector coding for RNA I and the primer RNA for initiation of DNA replication and their regulatory regions. Moreover, in accordance with this invention this DNA sequence is characterized by at least one modification that increases the copy number of the vector in an appropriate host as compared to a vector without that modification and further amplifies the expression of genes and DNA sequences under the control of the expression control sequence of the vector, i.e., above that amplification that results from the copy number increase. Although the particular high copy number and amplified expression sequence modification of this invention is not critical, in the preferred vectors of this invention the modification is a mutation at position 3029 (of pBR322), i.e., an exchange of a AT pair at that position for a GC pair. The modification may also be a temperature sensitive mutation or modification. Finally, in another embodiment of this invention, the modification is a deletion in the control region for the primer RNA of the vector.

There are various methods for causing and selecting this modification in the expression vectors of this invention. These are well known by those of skill in the art. Most usually, these methods depend on selecting high copy number modifications and then assaying these modifications to determine whether or not they also further amplify the expression of genes and DNA sequences under the control of the expression control sequences of the vectors of this invention. In the embodiment of this invention described herein, the mutation was a natural one. It was selected by monitoring the level of β-lactamase production in an ampicillin-sensitive *E. coli* host that had been made ampicillin-resistant by transformation with the parental vector.

While not wishing to be bound by theory, it is possible that the modifications of this invention, in addition to amplifying the copy number of the expression vector, also further amplify gene expression from promoters $P_I$ and $P_m$, thereby increasing the expression levels of genes and DNA sequences operatively linked to expression control sequences characterized by those promoters, by somehow strengthing those sequences or derepressing them in the host cells.

Finally, the expression vectors of this invention are characterized by at least one restriction site at which a gene or DNA sequence may be inserted into the vector and operatively linked therein to the expression control sequence of the vector. Such restriction sites are well known. They include for example AvaI, PstI, SalI, EcoRI, BamHI, HindIII and Sau3a. Methods for cleaving the vectors of this invention at that restriction site and inserting into that site a DNA sequence and operatively linking that sequence to the expression control sequence of the vector are also well-known.

METHODS FOR USING THE VECTORS OF THIS INVENTION

The DNA sequences that may be expressed by the vectors of this invention may be selected from a large variety of DNA sequences that encode prokaryotic or eukaryotic polypeptides. For example, such sequences may encode animal and human hormones, such as any of the various IFN-α's, particularly α2, α5, α6, α7, α8, IFN-β, IFN-γ, human insulin and growth hormone, bovine growth hormone, swine growth hormone and erythropoietin, human blood factors and plasminogen, viral or bacterial antigens, such as the core or surface antigen of HBV or the antigens of FMDV, and other useful polypeptides of prokaryotic or eukaryotic origin. Most preferably, the α-type interferons are used.

Methods for expressing these DNA sequences in the expression vectors of this invention and producing the polypeptides coded for by that sequence are well known. They include transforming an appropriate host with an expression vector having the desired DNA sequence operatively-linked to the expression control sequence of the vector, culturing the host under appropriate conditions of growth and collecting the desired polypeptide from the culture. It is most preferred that the host cells be allowed to reach stationary phase before the desired polypeptide is collected. Those of skill in the art may select from known methods those that are most effective for a particular gene expression without departing from the scope of this invention.

In order that this invention may be better understood, the following examples, for illustrative purposes only, are described.

METHODS AND MATERIALS

All restriction enzymes, polynucleotide kinase and T4 DNA ligase were purchased from New England Biolabs. Conditions for these enzymatic reactions have been described by N. Panayotatos and R. D. Wells, *J. Biol. Chem.*, 254, pp. 5555-61 (1979) and N. Panayotatos and R. D. Wells, *J. Mol. Biol.*, 135, pp. 91-109 (1979). DNA, as necessary, was prepared for subsequent reactions by ether extraction, followed by EtOH precipitation. Agarose and polyacrylamide gel electrophoresis were performed as described in Panayotatos and Wells, supra. "Fill-in" reactions with polymerase I-large fragment (Boehringer) ("Klenow") were carried out in 20 mM Tris-HCl (pH 7.6), 10 mM MgCl$_2$, 0.5 mM EDTA, 0.25 mM dithiothreitol and 60 mM each of the four deoxynucleotide triphosphates (Sigma) for 30 min at 37° C.

To determine β-lactamase activity, a 1 ml cell culture was treated with lysozyme at 0° C. for 30 min, followed by five freeze-thaw cycles. Increasing volumes of the lysed cell solution were added to cuvettes containing 50 μg/ml Nitrocefin (Glaxo Research Ltd.) in 0.1M phosphate buffer (pH 7.0). The increase in the absorbance at 482 mm with respect to time was followed spectrophotometrically. Initial rates were used to determine levels of β-lactamase activity.

EXAMPLE 1

Referring now to FIG. 1, we have depicted therein one embodiment of a method for producing and using an expression vector of this invention.

We restricted pVH51, a derivative of Col E1 [V. Hershfield et al., "Characterization Of A Mini-Col E1 Plasmid", *J. Bacteriol.*, 126, pp. 447-53 (1976); A. Oka, "Nucleotide Sequence Of Small Col E1 Derivatives: Structure Of The Regions Essential For Autonomous Replication And Colicin E1 Immunity", *Molec. gen. Genet.*, 172, pp. 151-59 (1979)] with AluI and isolated the blunt-end 255 base pair fragment carrying the $P_I$ promoter and part of the DNA sequence encoding RNA I by electrophoresis on a polyacrylamide gel (5%) (FIG. 1).

We then restricted pNKS-97 [N. Panayotatos and K. Truong, "Specific Deletion Of DNA Sequences Between Preselected Bases", *Nucleic Acids Research*, 9, pp. 5679-88 (1981)] with SalI, removed the overhanging ends with S1 and ligated the resulting fragment to a DNA fragment carrying the DNA sequence encoding IFN-α2 (FIG. 1). This construction does not regenerate the SalI site. Instead, it results in a construction having an ATG start codon (from the bacteriophage T7 fragment) attached to the TGT codon encoding the first amino acid of IFN-α2 (FIG. 1). The construction is also characterized by a Sau3A1 restriction site following the TGT codon of the first amino acid of IFN-α2. We designated this construction pNKS97-α2. Other DNA sequences encoding desired products may be inserted into the SalI site of pNKS97 in a like manner or using other methods well known in the art and employed as follows to practice this invention.

We next took pNKS97-α2 and restricted it with EcoRI, filled in the EcoRI residues with Klenow and dNTPs in a conventional manner and ligated to that filled-in site the blunt end AluI fragment, described above, in a conventional manner thereby regenerating the EcoRI site (FIG. 1).

This ligation produced a recombinant DNA molecule comprising an expression control sequence characterized by a $P_I$ promoter and a 112 bp fragment taken from the 14.7 to 15.0% region of bacteriophage T7 [Panayotatos and Truong, supra]; a DNA sequence within the replicon of the vector encoding RNA I and the primer RNA for initiation of DNA replication and their regulatory regions; and a DNA sequence encoding IFN-α2 operatively linked to the expression control sequence of the vector (FIG. 1). We designated this recombinant DNA molecule pP$_I$-T$_7$-α2.

We have also prepared vector pP$_I$-T$_7$ by isolating the 255 base pair AluI fragment of pVH51, as before, and ligating it to a fragment prepared by EcoRI restriction of pNKS97 and fill in of the overhanging ends with Klenow/dNTPs. This vector, not shown in FIG. 1, is characterized by an expression control sequence characterized by promoter $P_I$ and a DNA sequence from bacteriophage T$_7$; a DNA sequence within the replicon of the vector encoding RNA I and the primer RNA for initiation of DNA replication and their regulatory regions; and a SalI restriction site that permits DNA sequences encoding desired polypeptides to be inserted into the vector directly after the T7 region of the vector and the ATG start codon of that sequence so as to be operatively linked to promoter $P_I$.

We transformed *E. coli* HB101 with pP$_I$-T$_7$-α2 using conventional conditions and cultured the transformed hosts at pH 7.8, with slow shaking and very little aeration to produce interferon.* For example, in a shaker flask we used L-Broth (pH 7.8), shaking at 160-200 rpm and an almost full flask to reduce possible aeration. Yield: 30×10$^6$ units/OD/l.

*We have determined that pP$_I$-T$_7$-α2 has about 20 copies per cell.

To prepare a high copy mutant of pP$_I$-T$_7$-α2, we transformed *E. coli* K12 MO using conventional conditions and plated the cultures onto L-Broth/agar plates, supplemented with 20 mg/ml methicillin. We then selected some of the colonies that grew on those plates and plated them as before onto additional plates also supplemented with methicillin. We randomly selected colonies that grew on the second set of plates and tested them for β-lactamase production with nitrocefin (Glaxo). Colonies containing a high copy number of pP$_I$-T$_7$-α2 displayed a large red halo in that assay therefore allowing us to select a natural high copy mutant of that recombinant DNA molecule. We selected one of the high copy mutants and determined that its copy number was about 5× higher than the parental vector. The β-lactamse production of this mutant was, as expected, also about 5× higher than in the parental vector.

We then sequenced pP$_I$-T$_7$-α2 in the area of the natural mutation using conventional MaxamGilbert techniques and determined that the mutation appeared at position 3029 of the sequence (pBR322) where a GC base pair had replaced the former AT base pair (FIG. 1). This mutation is in the DNA sequence encoding RNA I. We designated this high copy mutant pP$_I$-T$_7$-α2 (cop$^-$) (FIG. 1).

Figure 4:
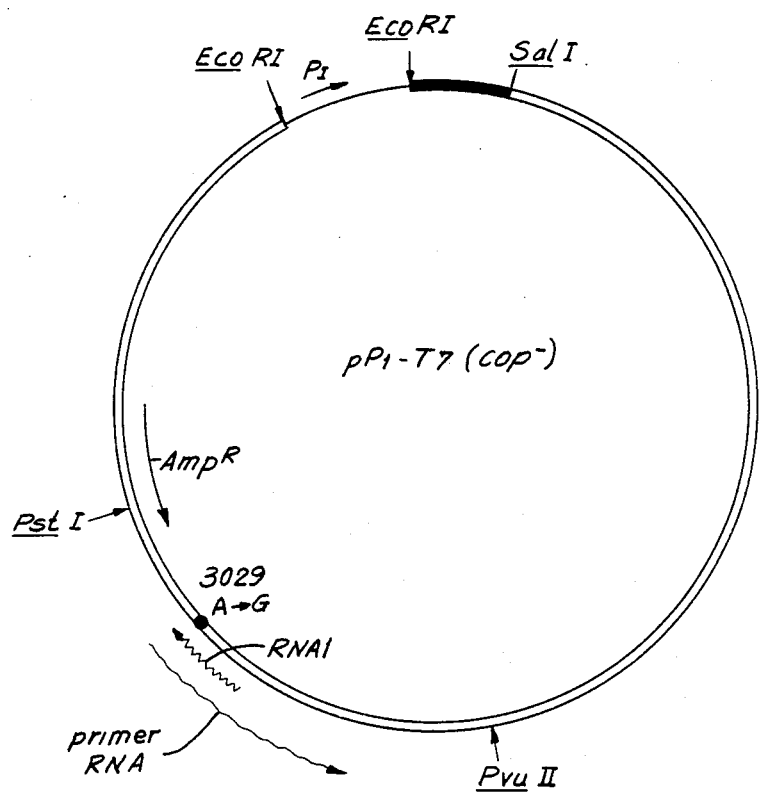
FIG. 4 is a schematic of $pP_I\text{-}T_7(\text{cop}^-)$, one of the expression vectors of this invention.

We have also prepared the same high copy mutant without the DNA sequence encoding IFN-α2 in substantially the same way using pP$_I$-T$_7$. This expression vector is designated pP$_1$-T$_7$ (cop$^-$). This expression vector, shown in FIG. 4, is characterized by an expression control sequence characterized by the $P_I$ promoter;

a DNA sequence within the replicon of the vector encoding RNA I and the primer RNA for initiation of DNA replication and their regulatory regions; this DNA sequence being characterized by a AT to GC base pair mutation at position 3029 (pBR322), this mutation increasing the copy number of the vector in an appropriate host as compared to a vector without the mutation and also further amplifying the expression of genes and DNA sequences under the control of the expression control sequence of the vector; and a SalI restriction site wherein a DNA sequence encoding a desired polypeptide may be inserted into the vector and operatively linked therein to the $P_I$ expression control sequence of that vector.

Figure 3:
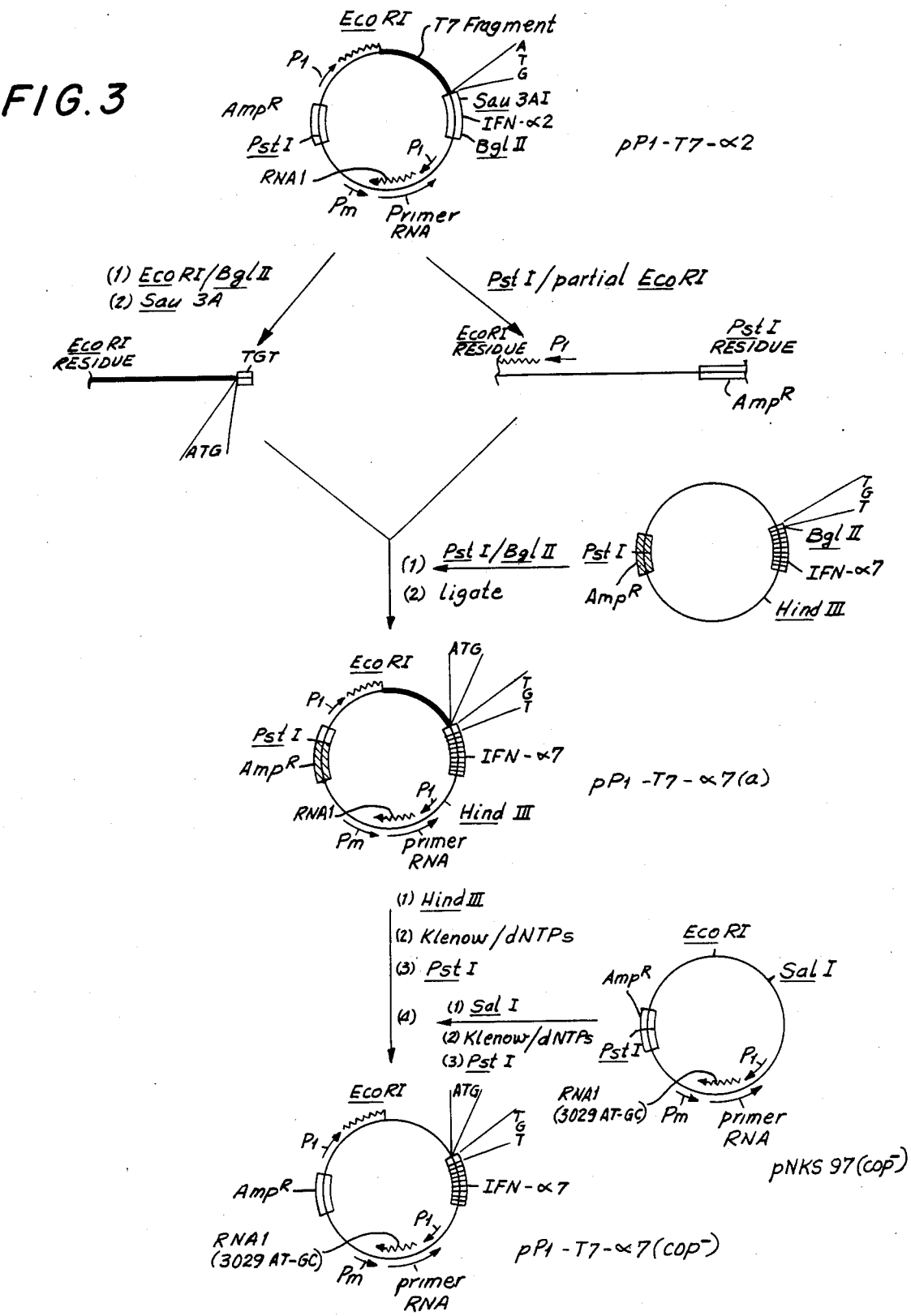
FIG. 3 is a schematic outline of another embodiment of making and using an expression vector of this invention.

Although $pP_I$-T7 (cop$^-$) may be used directly for inserting DNA sequences coding for desired polypeptides into the SalI site and operatively linking those DNA sequences to the expression control sequence of the vector, we prefer to insert the desired DNA sequences into the low copy parental plasmid $pP_I$-T7 and then to select the desired high copy and expression amplifying modification or to exchange the low copy control region for a cop$^-$ region previously selected in some other vector (e.g., FIG. 3).

We transformed *E. coli* HB101 with $pP_I$-T7-α2 (cop$^-$), using conventional conditions, and cultured it as before under conditions of slow growth (pH 7.8, 160–200 rpm, little aeration in a shaker flask or pH 7.8 in a fermenter).* Yield: 2–8 × 10$^9$ units/OD/l.

*It appears important that the growth of the transformed culture be slow in order to attain optimum yields. In a fermenter this is done merely by controlling the pH at about 7.8.

Therefore, the yield of interferon increased about 200 times using the high copy mutant, as compared to the interferon level produced using the parent strain. Since the copy number increase can only account for about a five times increase in gene expression (as it did for β-lactamase which is not under the control of promoter $P_I$), we believe that the expression vectors of our invention have in addition to increasing the copy number also further amplified gene expression from promoter $P_I$.

EXAMPLE 2

Figure 2:
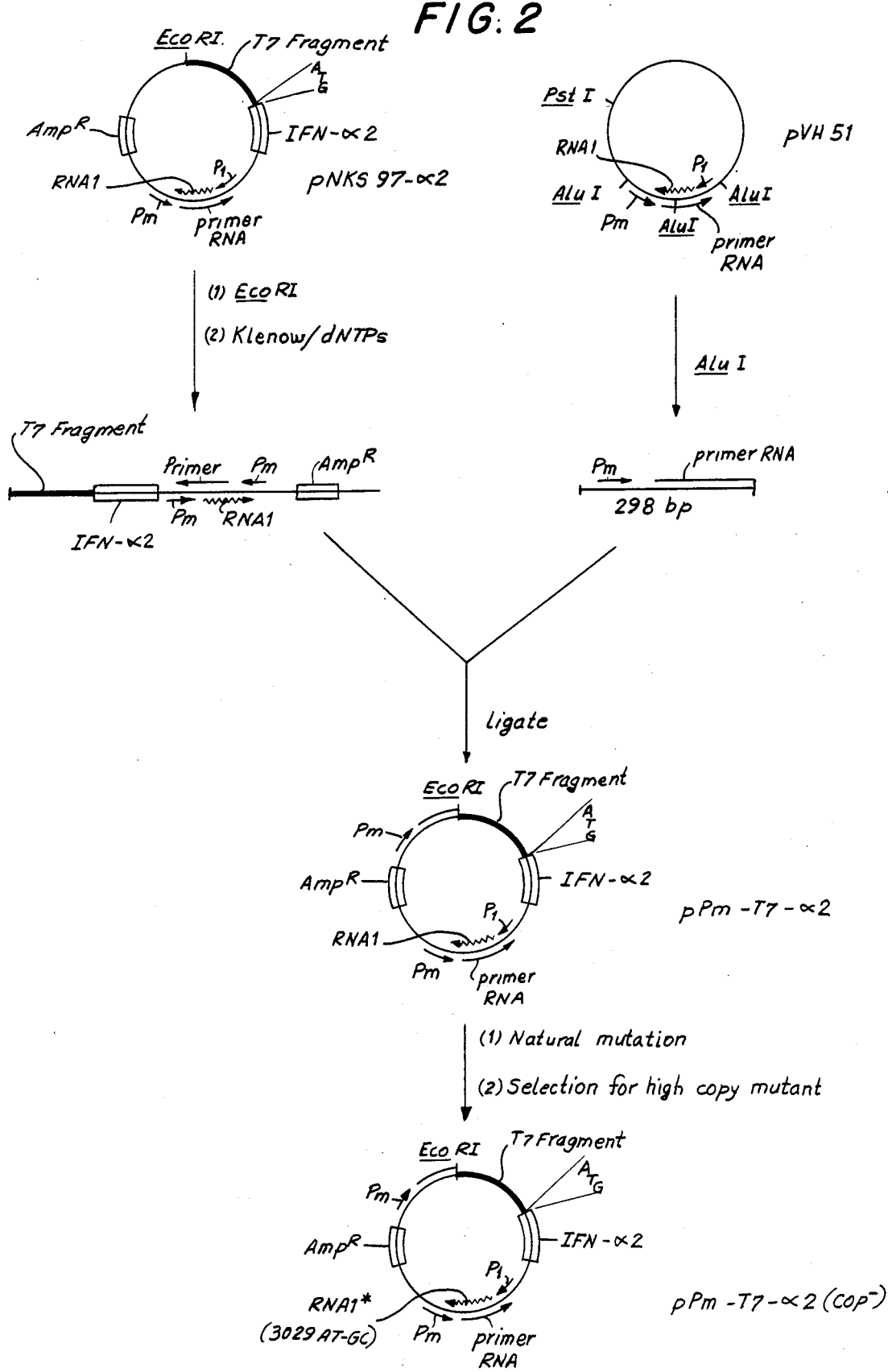
FIG. 2 is a schematic outline of another embodiment of making and using an expression vector of this invention.

Referring now to FIG. 2, we have depicted therein another embodiment of a method for producing and using an expression vector of this invention.

We again restricted pVH51 [Hershfield et al., supra] with AluI. This time we isolated the blunt-end 298 base pair fragment carrying the $P_m$ promoter and part of the DNA sequence encoding the primer RNA by electrophoresis as before. We then inserted this fragment into the EcoRI site of pNKS97-α2, as described previously, for the AluI fragment carrying $P_I$. We designated the resulting vector $pP_m$-T7-α2. On tranformation into *E. coli* HB101 and culturing as before, $pP_m$-T7-α2 produced interferon. Yield: 10 × 10$^6$ units/OD/l. Again, this plasmid had about 20 copies/cell. We have also prepared expression vector $pP_m$-T7, using substantially the same procedure described previously for $pP_I$-T7.

Figure 5:
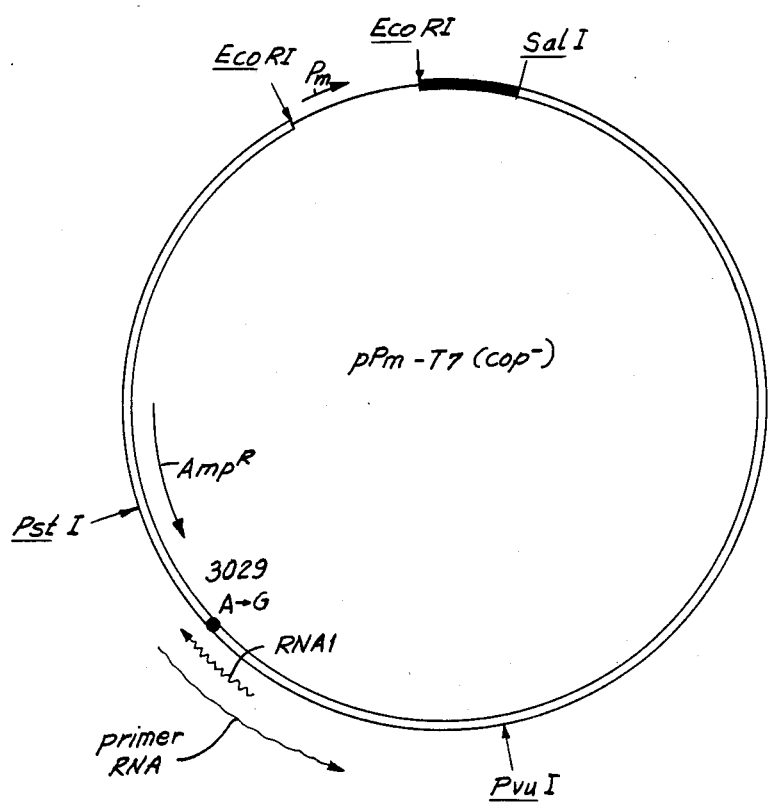
FIG. 5 is a schematic of $pP_m\text{-}T_7(\text{cop}^-)$, another of the expression vectors of this invention.

To obtain a high copy mutant of $pP_m$-T7-α2 (or $pP_m$-T7), we proceeded as before to select a natural mutation by growth on methicillin and selection using nitrocefin. Again, the mutant selected had substituted a GC base pair for the former AT base pair at position 3029 of pBR322.* We designated the high copy mutant, carrying the DNA sequence of IFN-α2: $pP_m$-T7-α2 (cop$^-$). We designated the high copy mutant of $pP_m$-T7: $pP_m$-T7 (cop$^-$). It is depicted in FIG. 5. Again, while $pP_m$-T7 (cop$^-$) may be used to insert DNA sequences directly into the SalI site, we prefer to employ the low copy parent vector for gene insertion and then to modify the resulting recombinant DNA molecule to the high copy and expression-amplifying modification by mutation or cloning (e.g., FIG. 3).

*Each time we selected a natural high copy mutant using this procedure, we isolated the identical mutant.

On transformation of *E. coli* HB101 and fermentation as before under conditions of slow growth, the transformed cells produced interferon. Yield: 0.7–3 × 10$^9$ units/OD/l. Again, the level of production of interferon using $pP_m$-T7-α2 (cop$^-$) was about 200× that of the parent strain. Since β-lactamase production (under the control of a different expression control sequence than IFN-α2 in the vector) increased only about 5× in $pP_m$-T7-α2 (cop$^-$), we again believe that the mutation in $pP_m$-T7-α2 (cop$^-$) acts both to increase the copy number and to increase the level of gene expression from $P_m$ in the vector.

EXAMPLE 3

Referring now to FIG. 3, we have depicted therein another embodiment of a method for producing and using an expression vector of this invention.

Since we have found it preferable to clone first a low copy number recombinant DNA molecule and then to modify that molecule to high copy number and amplified expression, we restricted $pP_I$-T7-α2, described previously, with EcoRI/BglII and Sau3AI and isolated the about 115 base pair EcoRI-Sau3AI fragment carrying the T7 sequences of $pP_1$-T7-α2 and the TGT codon encoding the first amino acid of IFN-α2 (FIG. 3).

We next restricted $pP_I$-T7-α2 with PstI and partially with EcoRI to isolate the EcoRI-PstI fragment carrying the $P_I$ promoter (FIG. 3). We employed this restriction strategy because of the multiple Sau3AI sites in the vector.

We then ligated these two fragments with a fragment encoding IFN-α7 (except for the TGT codon encoding its first amino acid). We generated the IFN-α7 fragment by restricting a pBR322-derived recombinant DNA molecule carrying IFN-α7 and characterized by a BglII site immediately following the TGT codon encoding the first amino acid of IFN-α7 (FIG. 3).* This triparte ligation resulted in reconstruction of the gene coding for ampicillin resistance (β-lactamase) and reconstruction of the gene coding for IFN-α7 (FIG. 3). Moreover, that gene coding for IFN-α7 is fused directly to the terminal ATG start codon of the T7 sequence of the vector and operatively linked there to promoter $P_I$. We designated this molecule $pP_I$-T7-α7(a) (FIG. 3). The "(a)" connotes that the sequence extending from the HindIII site to the PstI site carrying the replicon of the vector is not identical to that of $pP_I$-T7-α2, previously described, because that region in the PstI-BglII fragment carrying the IFN-α7 coding sequence was not identical to the corresponding region in $pP_I$-T7-α2.

*A BglII site is is complementary to a Sau3AI site.

In order to prepare the desired high copy mutant of $pP_I$-T7-α7(a) and to conform the sequence extending from the HindIII site to the PstI site carrying the replicon of the vector to that of $pP_I$-T7-α2 (cop$^-$)*, we restricted $pP_I$-T7 (cop$^-$)** with SalI, filled in the restriction residues with Klenow and dNTPs and restricted the fragment with PstI and isolated the PstI-SalI fragment carrying the RNA I cop$^-$ mutation (FIG. 3). We combined this fragment with a fragment prepared from $pP_I$-T7-α7 by HindIII restriction, fill-in with Klenow and dNTPs and PstI restriction (FIG. 3). This ligation resulted in the replacement of the low copy number region of pP$_I$-T$_7$-α7(a) with a high copy number mutant and made the region of the vector between the HindIII site and the PstI site identical to that of pP$_I$-T$_7$-α2 (cop⁻). We designated the resulting recombinant DNA molecule pP$_I$-T$_7$-α7 (cop⁻).

*This latter step was done merely to aid comparison of the resultant vector with pP$_I$-T$_7$-α2 (cop⁻). It is not required for use of the vector.
**We prepared pP$_I$-T$_7$ (cop⁻) by exchanging the PstI/AvaI fragments of pP$_I$-T$_7$ and pP$_I$-T$_7$-α2 (cop⁻). We as well could have obtained the desired cop⁻ fragment from pNKS97 (cop⁻), which may be prepared from pNKS97 by the methicillin and nitrocefin method described previously.

After transformation of *E. coli* HB101 and fermentation under the slow growth conditions, described previously, we assayed for IFN-α7 production. Yield: 1–4×10⁹ units/OD/l.

Microorganisms and vectors prepared by the processes described herein are exemplified by cultures deposited in the American Type Culture Collection, Rockville, Md. on Sept. 15, 1982 and there identified as follows:

| ATCC Accession Number | Culture |
|---|---|
| 39190 | *E. coli* MC 1061 (pP$_I$-T$_7$) |
| 39189 | *E. coli* MC 1061 (pP$_I$-T$_7$ (cop⁻)) |

While we have hereinbefore presented a number of embodiments of this invention, it is apparent that our basic construction may be altered to provide other embodiments which utilize the processes and compositions of this invention. Therefore, it will be appreciated that the scope of this invention is to be governed by the claims appended hereto rather than the specific embodiments which have been presented hereinbefore by way of example.

I claim:

1. An improved expression vector comprising an expression control sequence, said sequence comprising at least one promoter selected from the group consisting of a promoter of RNA I and a promoter of primer RNA for initiation of DNA replication; a DNA sequence within the replicon of the vector encoding RNA I and the primer RNA for initiation of DNA replication and their regulatory regions, said DNA sequence having an AT to GC mutation at position 3029 in the two strands of pBR322, said mutation increasing the copy number of the vector in a host as compared to a vector without such mutation and further amplifying the expression of genes and DNA sequences under the control of said expression control sequence of said vector beyond the amplification expected by the copy number increase; and at least one restriction site for insertion of a DNA sequence encoding a desired polypeptide into said vector and operatively linking the DNA sequence to said expression control sequence.

2. The expression vector of claim 1, wherein said expression control sequence also comprises DNA sequences coding for at least one of other promoters, operators or ribosome binding sites, including Shine Dalgarno sequences, and other expression related sequences.

3. The expression vector of claim 2, wherein said expression control sequence comprises DNA sequences coding for the ribosome binding sites, including the Shine Dalgarno sequences, of bacteriophage T$_7$.

4. The expression vector of claim 1, selected from the group consisting of pP$_I$-T$_7$ (cop⁻) and pP$_m$-T$_7$ (cop⁻).

5. The expression vector of claim 1, wherein said vector also includes a DNA sequence encoding a eukaryotic or prokaryotic polypeptide inserted into said vector at said restriction site and operatively linked therein to said expression control sequence.

6. The expression vector of claim 5, wherein said DNA sequence is selected from the group consisting of DNA sequences encoding animal and human hormones and viral and bacterial polypeptides.

7. The expression vector of claim 6, wherein said DNA sequence encodes polypeptides selected from the group consisting of human and animal interferons, human and animal growth hormones, antigens of foot and mouth disease virus, antigens of hepatitis B virus, human insulin, human blood factors and plasminogen activator, and erythropoietin.

8. A method for producing a polypeptide comprising the step of culturing a host transformed with a vector of one of claims 5 to 7.

* * * * *